United States Patent
Park et al.

(10) Patent No.: US 10,251,554 B2
(45) Date of Patent: Apr. 9, 2019

(54) MAGNETIC RESONANCE IMAGING APPARATUS AND METHOD OF GENERATING MAGNETIC RESONANCE IMAGE

(71) Applicant: SAMSUNG ELECTRONICS CO., LTD., Suwon-si (KR)

(72) Inventors: Sung-hun Park, Seoul (KR); Devadas Puthusseril, Kannur (IN); Jijeesh Koliyadan Veettil, Kannur (IN); Keum-yong Oh, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 656 days.

(21) Appl. No.: 14/824,519

(22) Filed: Aug. 12, 2015

(65) Prior Publication Data

US 2016/0047872 A1 Feb. 18, 2016

(30) Foreign Application Priority Data

Aug. 14, 2014 (KR) ........................ 10-2014-0106233

(51) Int. Cl.
*G01V 3/00* (2006.01)
*A61B 5/00* (2006.01)
(Continued)

(52) U.S. Cl.
CPC ............ *A61B 5/0037* (2013.01); *A61B 5/055* (2013.01); *A61B 5/748* (2013.01);
(Continued)

(58) Field of Classification Search
CPC ............ G01R 33/4816; G01R 33/4818; G01R 33/482; G01R 33/4822; G01R 33/4824;
(Continued)

(56) References Cited

U.S. PATENT DOCUMENTS

| 5,438,263 A | 8/1995 | Dworkin et al. |
| 6,108,573 A * | 8/2000 | Debbins ................. G01R 33/54 324/309 |

(Continued)

FOREIGN PATENT DOCUMENTS

| EP | 1220154 A2 | 7/2002 |
| JP | 2007136186 A | 6/2007 |

(Continued)

OTHER PUBLICATIONS

JP 2008018086 Machine Translation, Jan. 31, 2008.*

(Continued)

*Primary Examiner* — Giovanni Astacio-Oquendo
*Assistant Examiner* — Raul Rios Russo
(74) *Attorney, Agent, or Firm* — Sughrue Mion, PLLC

(57) ABSTRACT

An MRI apparatus includes: an image processor that generates a real-time image and a scout image by using an MR signal that is received from an object; a display that displays slices, which respectively correspond to portions of the object, on the scout image; and an input interface that receives a user input corresponding to at least one of the real-time image and the scout image. The image processor updates the real-time image based on the user input, and the display displays the updated real-time image.

21 Claims, 17 Drawing Sheets

(51) Int. Cl.
*A61B 5/055* (2006.01)
*G01R 33/54* (2006.01)
*G06T 19/00* (2011.01)
*G01R 33/48* (2006.01)
*G01R 33/483* (2006.01)

(52) U.S. Cl.
CPC ..... *G01R 33/4816* (2013.01); *G01R 33/4818* (2013.01); *G01R 33/546* (2013.01); *G06T 19/00* (2013.01); *A61B 5/7425* (2013.01); *G01R 33/482* (2013.01); *G01R 33/4835* (2013.01); *G06T 2219/008* (2013.01); *G06T 2219/028* (2013.01)

(58) Field of Classification Search
CPC ............ G01R 33/4826; G01R 33/4828; G01R 33/483; G01R 33/4831; G01R 33/4833; G01R 33/4835; G01R 33/4836; G01R 33/4838; G01R 33/387; G01R 33/246; G01R 33/38
USPC .................................................. 324/300–322
See application file for complete search history.

(56) References Cited

U.S. PATENT DOCUMENTS

| | | | |
|---|---|---|---|
| 6,898,302 B1 | 5/2005 | Brummer | |
| 8,217,648 B2 | 7/2012 | Kachi et al. | |
| 2002/0063560 A1* | 5/2002 | Debbins | G01R 33/54 324/307 |
| 2002/0082494 A1 | 6/2002 | Balloni et al. | |
| 2004/0161139 A1* | 8/2004 | Samara | G06F 17/30247 382/131 |
| 2006/0173268 A1* | 8/2006 | Mullick | A61B 5/055 600/407 |
| 2007/0127792 A1* | 6/2007 | Virtue | A61B 6/032 382/128 |
| 2009/0012383 A1* | 1/2009 | Virtue | A61B 6/032 600/407 |
| 2009/0209846 A1* | 8/2009 | Bammer | A61B 5/055 600/421 |
| 2014/0070809 A1* | 3/2014 | Imamura | G01R 33/36 324/319 |
| 2014/0098932 A1* | 4/2014 | Profio | A61B 6/032 378/19 |
| 2015/0199121 A1* | 7/2015 | Gulaka | G06F 3/04845 715/771 |
| 2015/0223771 A1* | 8/2015 | Lee | A61B 6/541 382/131 |

FOREIGN PATENT DOCUMENTS

| | | |
|---|---|---|
| JP | 200818086 A | 1/2008 |
| JP | 201094181 A | 4/2010 |

OTHER PUBLICATIONS

Communication dated May 11, 2016 issued by the Korean Intellectual Property Office in counterpart Korean Patent Application No. 10-2014-0106233.

Communication (PCT/ISA/210) dated Nov. 19, 2015, issued by the International Searching Authority in counterpart International Application No. PCT/KR2015/008385.

Communication dated Dec. 7, 2015, issued by the Korean Intellectual Property Office in counterpart Korean Application No. 10-2014-0106233.

Communication dated Jan. 28, 2016, issued by the European Patent Office in counterpart European Application No. 15180742.7.

* cited by examiner

MAGNETIC RESONANCE IMAGING APPARATUS AND METHOD OF GENERATING MAGNETIC RESONANCE IMAGE

CROSS-REFERENCE TO RELATED APPLICATION

This application claims priority from Korean Patent Application No. 10-2014-0106233, filed on Aug. 14, 2014, in the Korean Intellectual Property Office, the disclosure of which is incorporated herein in its entirety by reference.

BACKGROUND

1. Field

Apparatuses and methods consistent with exemplary embodiments relate to magnetic resonance imaging.

2. Description of the Related Art

A magnetic resonance imaging (MRI) apparatus captures an image of an object by using a magnetic field and may provide a three-dimensional (3D) view of a disc, a joint, a nerve, a ligand, etc., as well as a bone at a desired angle. MRI systems may acquire two-dimensional (2D) images or three-dimensional (3D) volume images that are oriented toward an optional point. Also, MRI systems may acquire images having high soft tissue contrast, and may acquire neurological images, intravascular images, musculoskeletal images, and oncologic images that are needed to capture abnormal tissues.

An MR image is obtained by acquiring a sectional image of a region of an object by expressing, in a contrast comparison, a strength of an MR signal generated in a magnetic field having a specific strength. The MR signal denotes an RF signal emitted from the object. For example, if an RF signal that only resonates a specific atomic nucleus (for example, a hydrogen atomic nucleus) is emitted toward the object placed in a magnetic field and then such emission stops, an MR signal is emitted from the specific atomic nucleus, and thus the MRI system may receive the MR signal and acquire an MR image. An intensity of the MR signal may be determined according to a density of a predetermined atom (for example, hydrogen) of the object, a relaxation time T1, a relaxation time T2, and a flow of blood or the like.

A user, for example, an operator or a radiologist, who uses the MRI apparatus may obtain the image by using the MRI apparatus.

Since the user of the MRI apparatus repeatedly manipulates the MRI apparatus, there is a need for the MRI apparatuses which are easy and convenient to use.

SUMMARY

One or more exemplary embodiments include an MRI apparatus that may be easily manipulated by an operator.

One or more exemplary embodiments include a method of generating an MR image which may enable an operator to relatively easily plan an imaging procedure.

According to one or more exemplary embodiments, an MRI apparatus includes: an image processor that generates a real-time image and a scout image by using a magnetic resonance (MR) signal that is received from an object; a display that displays slices, which respectively correspond to parts of the object, on the scout image; and an input interface that receives a first user input corresponding to at least one of the real-time image and the scout image, wherein the image processor updates the real-time image based on the first user input, and the display displays the updated real-time image.

For example, the display may display the slices such that a slice that is selected by the first user input is distinguished from non-selected slices.

For example, the display may display the slices on the scout image such that at least one among the slices is distinguished from other slices.

For example, the first user input may be a user input for adjusting at least one of positions, sizes, directions, and luminosities of the slices in the scout image.

For example, the scout image may include object images of a coil, a shim volume, and a saturator, wherein the display performs display so that an object image for a second user input is distinguished from other object images.

For example, the display may perform display by making a mark corresponding to an artifact on the scout image.

For example, when a specific absorption rate (SAR) or a peripheral nervous stimulus (PNS) that is measured when the real-time image is updated exceeds a reference value, the display may perform display by making a mark corresponding to the exceeding of the reference value on the scout image.

For example, the scout image may include a sagittal view image, a coronal view image, and an axial view image, wherein at least one of an arrangement and sizes of the sagittal view image, the coronal view image, and the axial view image is determined by the first user input.

For example, the scout image may include position information of a table that supports the object in the MRI apparatus.

For example, the image processor may adjust a brightness of a portion of the real-time image or the scout image to correspond to the first user input.

According to one or more exemplary embodiments, a method of generating an MR image includes: generating a real-time image and a scout image by using an MR signal that is received from an object; displaying slices, which respectively correspond to parts of the object, to correspond to the scout image; receiving a first user input corresponding to at least one of the real-time image and the scout image; updating the real-time image based on the first user input; and displaying the updated real-time image.

For example, the first user input may be an input for selecting at least one among the slices that are displayed to correspond to the scout image.

For example, a slice that is selected by the first user input may be displayed to be distinguished from non-selected slices.

For example, the displaying of the slices, which respectively correspond to the parts of the object, to correspond to the scout image may include displaying the slices so that at least one of the slices is distinguished from other slices.

For example, the displaying of the slices, which respectively correspond to the parts of the object, to correspond to the scout image may include displaying the slices so that at least one of lines for separating the slices is distinguished from other lines.

For example, a transparency, a color, and a shape of the at least one of the lines for separating the slices may be displayed to be different from those of the other lines.

For example, the first user input may be a user input for adjusting at least one of positions, sizes, directions, and luminosities of the slices in the scout image.

For example, the scout image may include object images of a coil, a shim volume, and a saturator, wherein when a second user input for one of the object images is received, the object image for the second user input is displayed to be distinguished from other object images.

For example, the second user input may be received through a shortcut key that is preset.

For example, the updating of the real-time image may include: obtaining the real-time image of a first slice; and displaying a portion of the scout image corresponding to the first slice to be distinguished from portions of the scout image corresponding to other slices.

For example, the first slice may be selected by the first user input.

For example, the displaying of the updated real-time image may include, when an artifact is detected in the updated real-time image, displaying the updated real-time image by making a mark corresponding to the artifact on the scout image.

For example, the displaying of the updated real-time image may include, when a specific absorption rate (SAR) or a peripheral nervous stimulus (PNS) that is measured when the real-time image is updated exceeds a reference value, displaying the updated real-time image by making a mark corresponding to the exceeding of the reference value on the scout image.

For example, the scout image may include a sagittal view image, a coronal view image, and an axial view image, and at least one of an arrangement and sizes of the sagittal view image, the coronal view image, and the axial view image is determined by the first user input.

For example, the scout image may include position information of a table that supports the object in an MRI apparatus.

For example, the updating of the real-time image may include adjusting a brightness of a portion of the real-time image or the scout image to correspond to the first user input.

According to one or more exemplary embodiments, an MRI apparatus includes: a display that displays a scout image including an image of slices corresponding to physical locations in an object and a real-time image corresponding to one of the slices; an input interface that receives a first user input which is a selection input for the one of the slices displayed on the scout image; and an image processor that updates the real-time image based on the first user input, and control the display to display the updated real-time image of the one of the slices.

For example, the display may display the slices on the scout image such that the one of the slices that is selected by the first user input is distinguished from non-selected slices.

For example, at least one of a position, a direction, a size, and a luminosity of the one of the slices in the scout image may be changed in response to receiving the first user input, and the image processor may update the real-time image based on a change in at least one of the position, the direction, the size, and the luminosity of the one of the slices.

For example, the scout image includes a sagittal view image, a coronal view image, and an axial view image which are displayed in a first arrangement, the input interface may receive a second user input with respect to the scout image, and the first arrangement may be changed by the second user input so that the sagittal view image, the coronal view image, and the axial view image are displayed in a second arrangement in which at least one of a position and a size of at least one of the sagittal view image, the coronal view image, and the axial view image is changed as compared to the first arrangement.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
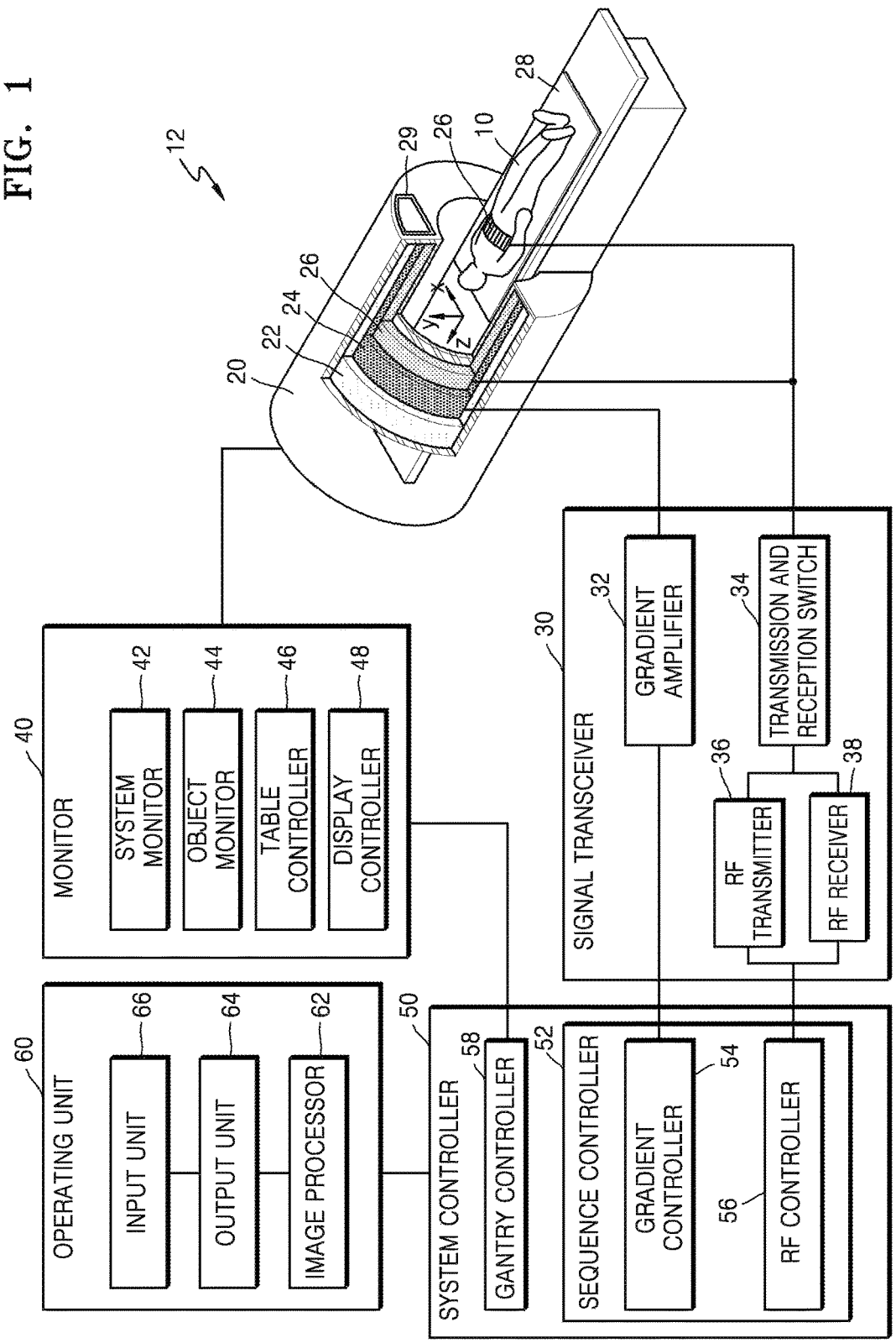
FIG. 1 is a block diagram of an MRI system.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions are not described in detail since they would obscure the description with unnecessary detail.

As used herein, the term "and/or" includes any and all combinations of one or more of the associated listed items. Expressions such as "at least one of" when preceding a list of elements, modify the entire list of elements and do not modify the individual elements of the list.

When a part "includes" or "comprises" an element, unless there is a particular description contrary thereto, the part can further include other elements, not excluding the other elements. Also, the term "unit" in the exemplary embodiments means a software component or hardware component such as a field-programmable gate array (FPGA) or an application-specific integrated circuit (ASIC), and performs a specific function. However, the term "unit" is not limited to software or hardware. The "unit" may be formed to be in an addressable storage medium, or may be formed to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Throughout the specification, an "image" may denote multi-dimensional data composed of discrete image elements (for example, pixels in a two-dimensional image and voxels in a three-dimensional image). For example, the image may be a medical image of an object captured by an X-ray apparatus, a computed tomography (CT) apparatus, an MRI apparatus, an ultrasound apparatus, or another medical imaging apparatus.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. Furthermore, the "object" may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, a medical imaging expert, or a technician who repairs a medical apparatus.

Furthermore, in the present specification, an MR image is an image of an object obtained by using the nuclear magnetic resonance principle.

Furthermore, in the present specification, a "pulse sequence" refers to continuity of signals repeatedly applied by an MRI apparatus. The pulse sequence may include a time parameter of a radio frequency (RF) pulse, for example, repetition time (TR) or echo time (TE).

Furthermore, in the present specification, a "pulse sequence schematic diagram" shows an order of events that occur in an MRI apparatus. For example, the pulse sequence schematic diagram may be a diagram showing an RF pulse, a gradient magnetic field, an MR signal, or the like according to time.

FIG. 1 is a block diagram of an MRI apparatus 12. Referring to FIG. 1, the MRI apparatus may include a gantry 20, a signal transceiver 30, a monitor 40, a system controller 50, and an operating unit 60.

The gantry 20 includes a main magnet 22, a gradient coil 24, and an RF coil 26. A magnetostatic field and a gradient magnetic field are formed in a bore in the gantry 20, and an RF signal is emitted toward an object 10.

The main magnet 22, the gradient coil 24, and the RF coil 26 may be arranged in a predetermined direction of the gantry 20. The predetermined direction may be a coaxial cylinder direction. The object 10 may be disposed on a table 28 that is capable of being inserted into a cylinder along a horizontal axis of the bore.

The main magnet 22 generates a magnetostatic field for aligning magnetic dipole moments of atomic nuclei of the object 10 in a constant direction. An accurate MR image of the object 10 may be obtained due to a strong uniform magnetic field generated by the main magnet 22.

The gradient coil 24 includes X, Y, and Z coils for generating gradients in X-, Y-, and Z-axis orthogonal directions. The gradient coil 24 may provide position information of each region of the object 10 by differently inducing resonant frequencies according to the regions of the object 10.

The RF coil 26 may emit an RF signal toward an object and receive an MR signal emitted from the object. In detail, the RF coil 26 may transmit, toward atomic nuclei included in the object and having precessional motion, an RF signal having the same frequency as that of the precessional motion, stop transmitting the RF signal, and then receive an MR signal emitted from the atomic nuclei included in the object.

For example, in order to transit an atomic nucleus from a low energy state to a high energy state, the RF coil 26 may generate and apply an electromagnetic wave signal that is an RF signal corresponding to a type of the atomic nucleus, to the object 10. When the electromagnetic wave signal generated by the RF coil 26 is applied to the atomic nucleus, the atomic nucleus may transit from the low energy state to the high energy state. Then, when electromagnetic waves generated by the RF coil 26 disappear, the atomic nucleus to which the electromagnetic waves were applied transits from the high energy state to the low energy state, thereby emitting electromagnetic waves having a Larmor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Larmor frequency. The RF coil 26 may receive electromagnetic wave signals from atomic nuclei included in the object 10.

The RF coil 26 may be a single RF transmit and receive coil having both a function of generating electromagnetic waves each having an RF that corresponds to a type of an atomic nucleus and a function of receiving electromagnetic waves emitted from an atomic nucleus. Alternatively, the RF coil 26 may include a separate transmit RF coil having a function of generating electromagnetic waves each having an RF that corresponds to a type of an atomic nucleus, and a separate receive RF coil having a function of receiving electromagnetic waves emitted from an atomic nucleus.

The RF coil 26 may be fixed to the gantry 20 or may be detachable. When the RF coil 26 is detachable, the RF coil 26 may include one or more coils for a part of the object, such as a head coil, a chest coil, a leg coil, a neck coil, a shoulder coil, a wrist coil, an ankle coil, etc.

The RF coil 26 may communicate with an external apparatus via wires and/or wirelessly, and may also perform dual tune communication according to a communication frequency band.

The RF coil 26 may be an RF coil having various numbers of channels, such as 16 channels, 32 channels, 72 channels, and 144 channels.

The gantry 20 may include a display 29 disposed outside the gantry 20 and a display (not shown) disposed inside the gantry 20. The gantry 20 may provide predetermined information to the user or the object 10 through the display 29 and/or the display disposed inside the gantry 20.

The signal transceiver 30 may control the gradient magnetic field formed inside the gantry 20, i.e., in the bore, according to a predetermined MR sequence, and control transmission and reception of an RF signal and an MR signal.

The signal transceiver 30 may include a gradient amplifier 32, a transmission and reception switch 34, an RF transmitter 36, and an RF receiver 38.

The gradient amplifier 32 drives the gradient coil 24 included in the gantry 20, and may supply a pulse signal for generating a gradient to the gradient coil 24 under the control of a gradient controller 54. By controlling the pulse signal supplied from the gradient amplifier 32 to the gradient coil 24, gradients in X-, Y-, and Z-axis directions may be synthesized.

The RF transmitter 36 and the RF receiver 38 may drive the RF coil 26. The RF transmitter 36 may supply an RF pulse in a Larmor frequency to the RF coil 26, and the RF receiver 38 may receive an MR signal received by the RF coil 26.

The transmission and reception switch 34 may adjust transmitting and receiving directions of the RF signal and the MR signal. For example, the transmission and reception switch 34 may emit the RF signal toward the object 10 through the RF coil 26 during a transmission mode, and receive the MR signal from the object 10 through the RF coil 26 during a reception mode. The transmission and reception switch 34 may be controlled by a control signal output by an RF controller 56.

The monitor 40 may monitor or control the gantry 20 or devices mounted on the gantry 20. The monitor 40 may include a system monitor 42, an object monitor 44, a table controller 46, and a display controller 48.

The system monitor 42 may monitor and control a state of the magnetostatic field, a state of the gradient magnetic field, a state of the RF signal, a state of the RF coil 26, a state of the table 28, a state of a device measuring body information of the object 10, a power supply state, a state of a thermal exchanger, and a state of a compressor.

The object monitor 44 monitors a state of the object 10. In detail, the object monitor 44 may include a camera for observing a movement or position of the object 10, a respiration measurer for measuring the respiration of the object 10, an electrocardiogram (ECG) measurer for measuring the cardiac activity of the object 10, or a temperature measurer for measuring a temperature of the object 10.

The table controller 46 controls a movement of the table 28 where the object 10 is positioned. The table controller 46 may control the movement of the table 28 according to a sequence control of a sequence controller 52. For example, during moving imaging of the object 10, the table controller 46 may continuously or discontinuously move the table 28 according to the sequence control of the sequence controller 52, and thus the object 10 may be imaged in a field of view (FOV) larger than that of the gantry 20.

The display controller 48 controls the display 29 disposed outside the gantry 20 and the display disposed inside the gantry 20 to be on or off, and may control a screen image to be output on the display 29 and the display disposed inside the gantry 20. Also, when a speaker is located inside or outside the gantry 20, the display controller 48 may control the speaker to be on or off, or may control sound to be output via the speaker.

The system controller 50 may include the sequence controller 52 for controlling a sequence of signals transmitted to the gantry 20, and a gantry controller 58 for controlling the gantry 20 and the devices mounted on the gantry 20.

The sequence controller 52 may include the gradient controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating unit 60. The pulse sequence may include information to control the gradient amplifier 32, the RF transmitter 36, the RF receiver 38, and the transmission and reception switch 34. For example, the pulse sequence may include information about a strength, an application time, and application timing of a pulse signal applied to the gradient coil 24.

The operating unit 60 may request the system controller 50 to transmit pulse sequence information while controlling an overall operation of the MRI apparatus.

The operating unit 60 may include an image processor 62 for receiving and processing the MR signal received by the RF receiver 38, an output unit 64, and an input unit 66.

The image processor 62 may process the MR signal received from the RF receiver 38 to generate MR image data of the object 10.

The image processor 62 receives the MR signal received by the RF receiver 38 and performs any one of various signal processes, such as amplification, frequency transformation, phase detection, low frequency amplification, and filtering, on the received MR signal.

The image processor 62 may arrange digital data in a k space of a memory, and rearrange the digital data into image data via 2D or 3D Fourier transformation.

The image processor 62 may perform a composition process or a difference calculation process on the image data. The composition process may include an addition process on a pixel or a maximum intensity projection (MIP) process. The image processor 62 may store the rearranged image data and the image data on which a composition process or a difference calculation process is performed, in a memory (not shown) or an external server.

The image processor 62 may perform any of the signal processing on the MR signal in parallel. For example, the image processor 62 may perform a signal processing on a plurality of MR signals received by a multi-channel RF coil in parallel to rearrange the plurality of MR signals into image data.

The output unit 64 may output image data generated or rearranged by the image processor 62 to the user. The output unit 64 may also output information required for the user to manipulate the MRI apparatus, such as a user interface (UI), user information, or object information. The output unit 64 may include at least one of a speaker, a printer, a cathode-ray tube (CRT) display, a liquid crystal display (LCD), a plasma display panel (PDP) display, an organic light-emitting diode (OLED) display, a field emission display (FED), a light-emitting diode (LED) display, a vacuum fluorescent display (VFD), a digital light processing (DLP) display, a flat panel display (FPD), a 3D display, a transparent display, or any one of other various output devices that are known to one of ordinary skill in the art.

The user may input object information, parameter information, a scan condition, a pulse sequence, or information about image composition or difference calculation by using the input unit 66. The input unit 66 may include at least one of a keyboard, a mouse, a track ball, a voice recognizer, a gesture recognizer, a touch screen, or any one of other various input devices that are known to one of ordinary skill in the art.

Although the signal transceiver 30, the monitor 40, the system controller 50, and the operating unit 60 are shown as separate components in FIG. 1, this is not limiting and respective functions of at least one of the signal transceiver 30, the monitor 40, the system controller 50, and the operating unit 60 may be performed by one integrated component. For example, the image processor 62 may convert the MR signal received from the RF receiver 38 into a digital signal in FIG. 1, but alternatively, the conversion of the MR signal into the digital signal may be performed by the RF receiver 38 or the RF coil 26.

The gantry 20, the RF coil 26, the signal transceiver 30, the monitor 40, the system controller 50, and the operating unit 60 may be connected to each other by wire or wireless sly, and when they are connected wireless sly, the MRI apparatus may further include an apparatus (not shown) for synchronizing clock signals therebetween. Communication between the gantry 20, the RF coil 26, the signal transceiver 30, the monitor 40, the system controller 50, and the operating unit 60 may be performed by using a high-speed digital interface, such as low voltage differential signaling (LVDS), asynchronous serial communication, such as a universal asynchronous receiver transmitter (UART), a low-delay network protocol, such as error synchronous serial communication or a controller area network (CAN), optical communication, or any of other various communication methods that are known to one of ordinary skill in the art.

Figure 2:
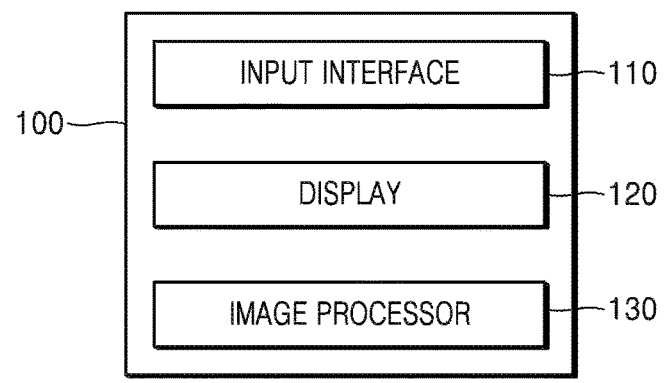
FIG. 2 is a block diagram illustrating an MRI apparatus according to an exemplary embodiment.
Figure 3:
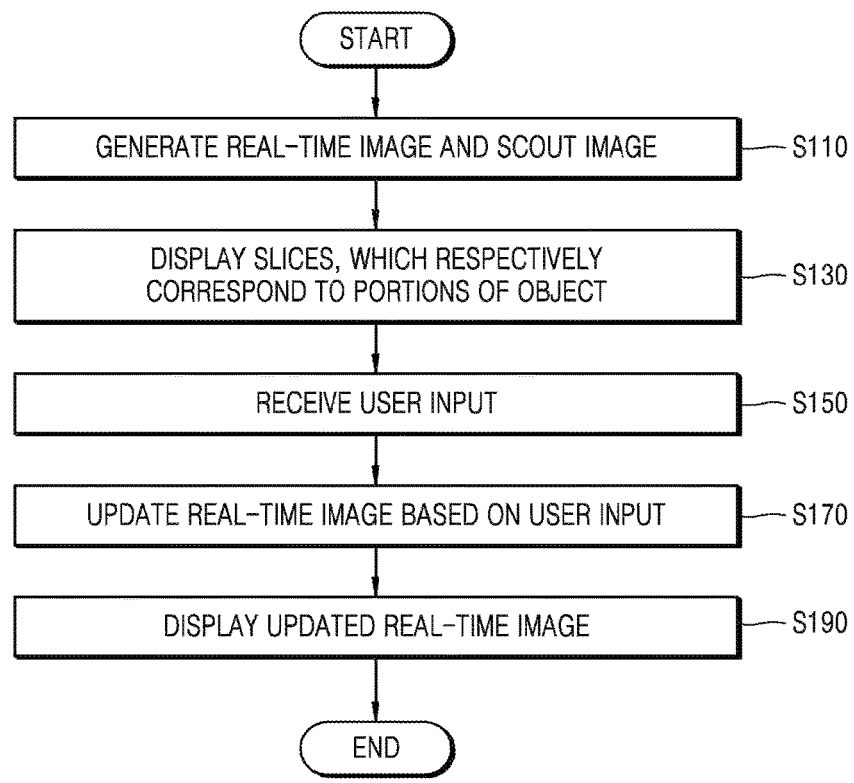
FIG. 3 is a flowchart of a method performed by the MRI apparatus to generate an MR image, according to an exemplary embodiment.
Figure 4:
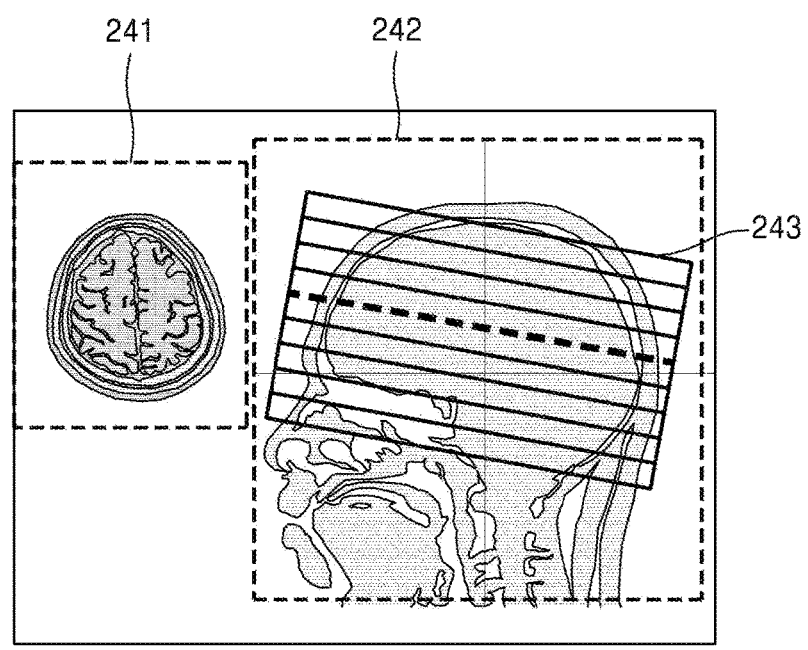
FIG. 4 is a view illustrating a real-time image and a scout image according to an exemplary embodiment.

FIG. 2 is a block diagram illustrating an MRI apparatus 100 according to an exemplary embodiment, FIG. 3 is a flowchart of a method performed by the MRI apparatus 100 to generate an MR image, according to an exemplary embodiment, and FIG. 4 is a view illustrating the real-time image 241 and the scout image 242 according to an exemplary embodiment.

The MRI apparatus 100 may include an input interface 110, a display 120, and an image processor 130.

The input interface 110, the display 120, and the image processor 130 may respectively correspond to the input unit 66, the output unit 64, and the image processor 62 of FIG. 1 and, thus, the described above is applicable here.

The image processor 130 may generate an MR image of an object by processing an MR signal that is received from the object.

The image processor 130 according to an exemplary embodiment may generate at least one of a real-time image and a scout image by using the MR signal that is received from the object. For example, the real-time image may refer to an MR image that is generated when the MR signal is simultaneously received and processed, e.g., a real-time image 241 of FIG. 4. The real-time image 241 may refer to an MR image that is generated without delay when the MRI apparatus 100 receives an MR signal.

An operator may see the real-time image 241 and may determine whether the real-time image 241 is an image for the current MR signal. The real-time image may be referred to as a live image, a real-time view, or a live view.

For example, the scout image may refer to an image for planning an imaging procedure of the object, e.g., a scout image 242 of FIG. 4. Also, the scout image may refer to an image for causing the object to correspond to each slice for the imaging procedure.

For example, the scout image may be generated by using a part of the received MR signal. The scout image may be referred to as an exam image, an exam view, a planning image, or a planning view.

The image processor 130 may update the real-time image based on a user input. The image processor 130 may receive the user input through the input interface 110 and may update the real-time image by using any of various methods.

The user input may refer to a user input for adjusting at least one of positions, sizes, directions, and luminosities of slices that are included in the scout image.

The image processor 130 may adjust a brightness of a portion of the real-time image or the scout image to correspond to the user input.

The display 120 may display, to a user, image data that is generated or reconstructed by the image processor 130. Also, the display 120 may display a graphical user interface (GUI), and may display information such as user information or object information in order for the user to manipulate an MRI apparatus. The display 120 may include one or more displays described above with reference to FIG. 1.

The display 120 according to an exemplary embodiment may display at least one of the scout image and the real-time image.

The display 120 according to an exemplary embodiment may display, on the scout image, slices that respectively correspond to parts of the object. The display 120 may display the real-time image that is updated by the image processor 130 based on the user input.

The display 120 according to an exemplary embodiment may perform display so that a slice that is selected by the user input is distinguished from non-selected slices.

The display 120 according to an exemplary embodiment may perform display on the scout image so that at least one of the slices is distinguished from other slices.

The display 120 according to an exemplary embodiment may perform display by making a mark corresponding to an artifact on the scout image.

When a specific absorption rate (SAR) or a peripheral nervous stimulus (PNS) that is measured when the real-time image is updated exceeds a reference value, the display 120 according to an exemplary embodiment may perform display by making a mark corresponding to the exceeding of the reference value.

The input interface 110 may receive the user input by using any of various methods from the user.

For example, the input interface 110 may include a unit used by the user to input data to control the MRI apparatus 100. For example, the input interface 110 may include at least one of a keypad, a dome switch, a touchpad (e.g., a capacitive overlay touchpad, a resistive overlay touchpad, an infrared touchpad, a surface acoustic wave touchpad, an integral strain gauge touchpad, or a piezoelectric touchpad), a jog wheel, or a jog switch. Also, the input interface may include a touch screen, a touch panel, a microphone, or a keyboard.

Also, the input interface 110 may include at least one module for receiving data from the user. For example, the input interface 110 may include a motion recognition module, a touch recognition module, and/or a voice recognition module.

The touch recognition module may detect the user's touch gesture on a touch screen and may transmit information about the touch gesture to a processor. The voice recognition module may recognize the user's voice by using a voice recognition engine and may transmit the recognized voice to the processor. The motion recognition module may recognize a motion of the object to be input and may transmit information about the motion of the object to the processor.

An input of the user through the input interface 110 of the MRI apparatus 100 may include at least one of a touch input, a bending input, a voice input, a key input, and a multimodal input.

The input interface 110 according to an exemplary embodiment may receive the user input corresponding to the real-time image and the scout image.

For example, the input interface 110 may receive a command to select a slice which the user inputs through a touch input. For example, the input interface 110 may receive a command to select a line of a slice which the user inputs through a click input on the scout image.

For example, the input interface 110 may receive an input for a position or a size of a slice which the user input through a drag and drop input on the scout image.

For example, the input interface 110 may receive a command, which the user inputs through a touch input or a selection input, to select a line among a plurality of lines that are displayed on the scout image.

The input interface 110 may receive a selection input or a position change input for the coil, the shim volume, and the saturator that are displayed on the scout image, as described below in detail with reference to FIG. 8.

Referring to FIG. 3, in operation S110, the image processor 130 may generate a real-time image and a scout image by using an MR signal that is received from an object. The real-time image may refer to an MR image that is generated without delay when the MRI apparatus 100 receives the MR signal. An operator may see the real-time image and may determine whether the real-time image is an image for the current MR signal.

The scout image may refer to an image for planning an imaging procedure of the object. The scout image may be a screen obtained by temporarily capturing the real-time image in order to plan the imaging procedure of the object.

In operation S130, the display 120 may display slices that respectively correspond to parts of the object to correspond to the scout image. The display 120 may simultaneously display an image of the object and an image of the slices in the scout image 242 of FIG. 4. The display 120 may display the image of the slices on the image of the object so that a user may edit the slices corresponding to the object by using any of various input units.

In operation S150, the input interface 110 may receive a user input corresponding to the real-time image and the scout image.

For example, the input interface 110 may be a touch screen. The input interface 110 may provide an image of slices 243 so that the operator may select any of the slices 243. When the input interface 110 receives an input by which the user touches any of the slices 243, the display 120 may display the real-time image of the slice 243.

When the input interface 110 receives an input by which the user clicks any of the slices 243, the display 120 may differently display an image of the slice 243 on a portion of the real-time image.

In operation S170, the image processor 130 may update the real-time image based on the user input.

The image processor 130 may update the real-time image to correspond to an input made by the user through the input interface 110. For example, when the input interface 110 receives an input by which the user changes a size of any of the slices 243, the image processor 130 may update the real-time image to correspond to the changed size of the slice 243.

In operation S190, the display 120 may display the updated real-time image.

The display 120 may display the real-time image that is updated according the user input received by the image processor 130.

For example, the display 120 may perform display by making a mark on an updated portion so that the updated portion is distinguished from non-updated portions. For example, the display 120 may display additional information (for example, slice information) of the updated portion along with the real-time image For example, the display 120 may perform display so that an image that is previously output and an image that is currently output are distinguished from each other. For example, the display 120 may perform display so that slice information of the image that is previously output and slice information of the image that is currently output are distinguished from each other. For example, the display 120 may perform display on the scout image so that a slice corresponding to the updated portion in the real-time image is distinguished from other slices.

For example, the display 120 may perform display on the scout image to which part of the object the real-time image corresponds. For example, the display 120 may display a part of the object, which is displayed on the real-time image, on the scout image. For example, the display 120 may display a portion corresponding to a part of the object, which is displayed on the real-time image, on a slice that is included in the scout image.

Figure 5:
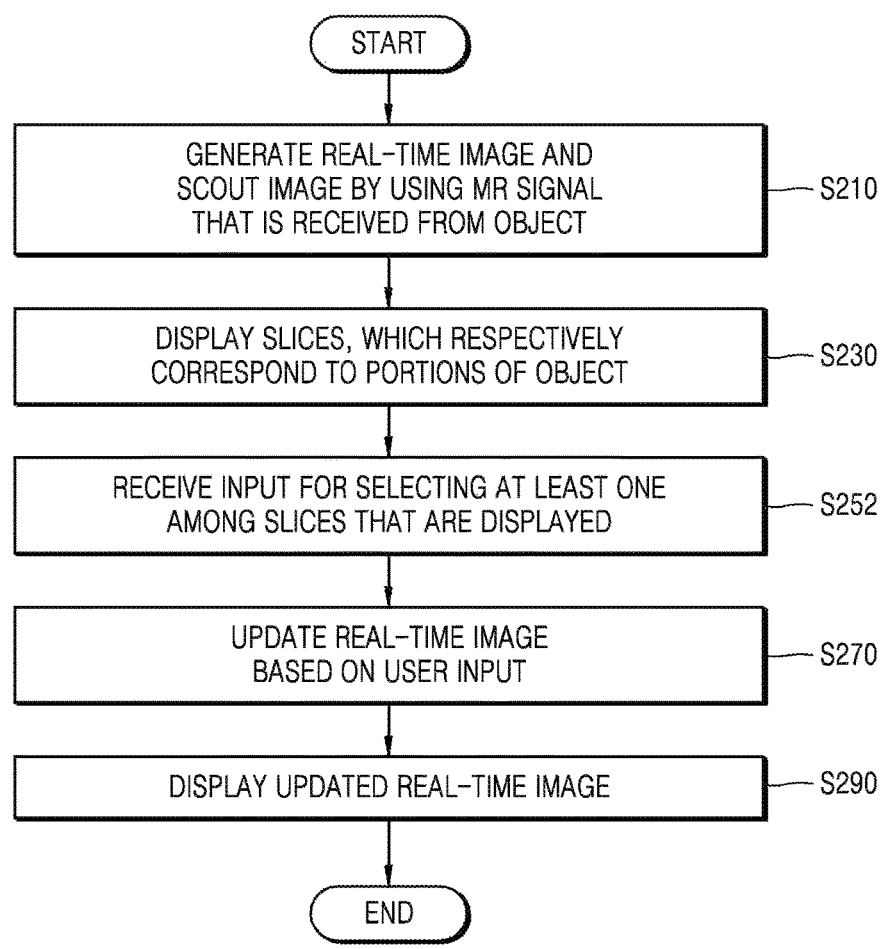
FIG. 5 is a flowchart of a method performed by the MRI apparatus to generate an MR image, according to an exemplary embodiment.

FIG. 5 is a flowchart of a method performed by the MRI apparatus 100 to generate an MR image, according to an exemplary embodiment.

Operations S210, S230, S270, and S290 of FIG. 5 are respectively the same as operations S110, S130, S170, and S190 of FIG. 3, and thus a repeated explanation thereof will be omitted.

Referring to FIGS. 4 and 5, in operation S210, the image processor 130 may generate the real-time image 241 and the scout image 242 by using an MR signal that is received from an object. In operation S230, the display 120 may display the slices 243 that respectively correspond to parts of the object to correspond to the scout image 242.

In operation S252, the input interface 110 may receive an input by which at least one of the slices 243 that are displayed to correspond to the real-time image and the scout image is selected.

The input interface 110 may provide an image of the slices 243 so that an operator may select the at least one slice 243. When the input interface 110 receives an input by which a user touches a slice, the display 120 may display the real-time image of the slice.

The input interface 110 may provide the real-time image 241 or the scout image 242 so that the operator may select the at least one slice 243. When the input interface 110 receives an input by which the user locks the slice 243, the display 120 may differently display an image of the slice 243 on a portion of the real-time image.

In operation S270, the image processor 130 may update the real-time image 241 based on a user input. In operation S290, the display 120 may display the updated real-time image.

Figure 6:
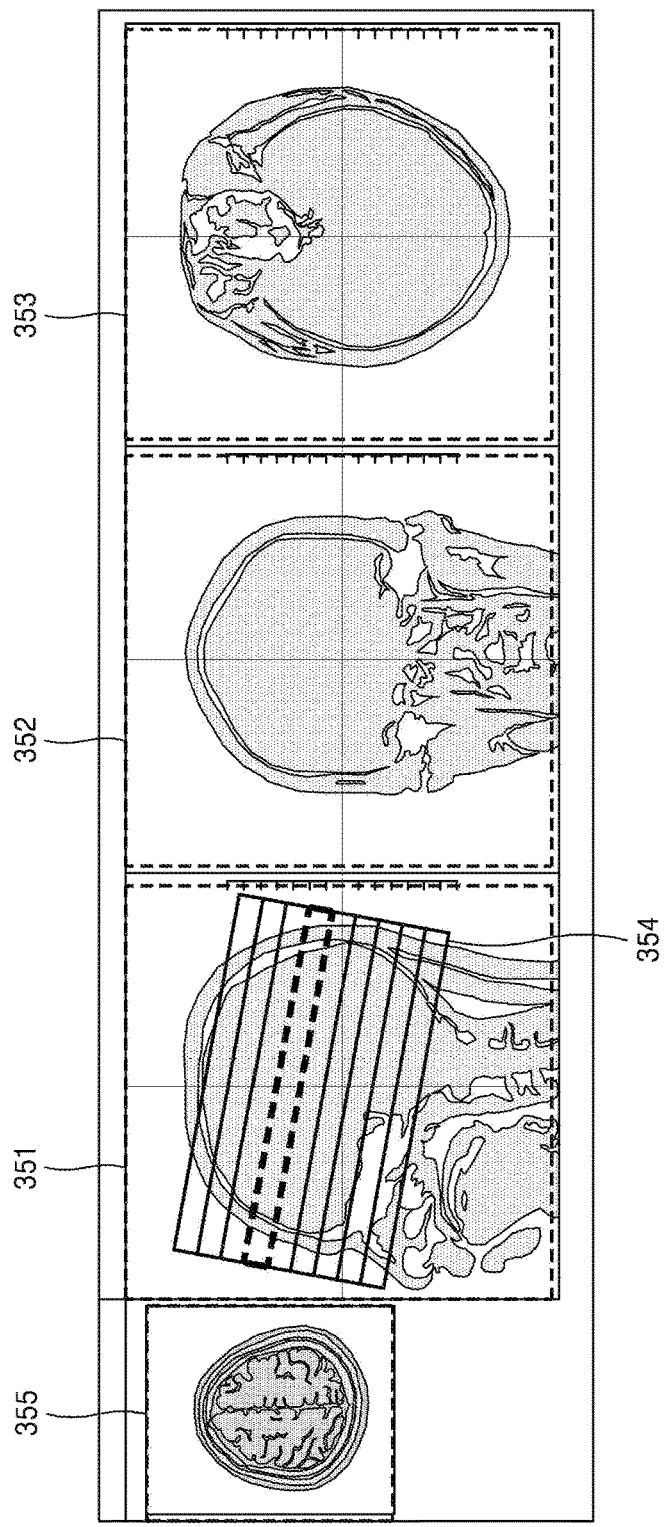
FIG. 6 is a view illustrating a real-time image and scout images according to an exemplary embodiment.

FIG. 6 is a view illustrating a real-time image 355 and scout images according to an exemplary embodiment.

The scout images may respectively include a sagittal view image 351, a coronal view image 352, and an axial view image 353. For example, the sagittal view image 351 may include a plurality of slices 354 of an object. For example, when a user selects a slice, the selected slice may be displayed so that at least one of a transparency, a color, and a shape of the selected slice are different from those of other slices. For example, the selected slice may be indicated by a dashed line as shown in FIG. 6.

Figure 7:
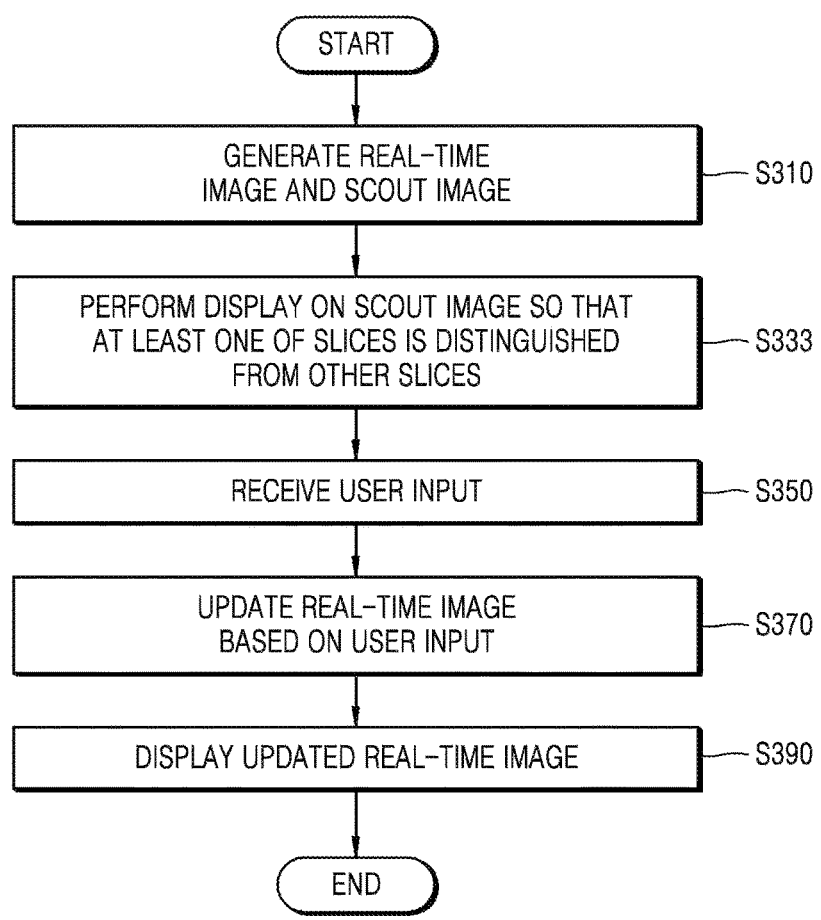
FIG. 7 is a flowchart of a method performed by the MRI apparatus to generate an MR image, according to an exemplary embodiment.

FIG. 7 is a flowchart of a method performed by the MRI apparatus 100 to generate an MR image, according to an exemplary embodiment.

Operations S310, S350, S370, and S390 of FIG. 7 are respectively the same as operations S110, S150, S170, and S190 of FIG. 6, and thus a repeated explanation thereof will be omitted.

Referring to FIGS. 6 and 7, in operation S310, the image processor 130 may generate the real-time image 355 and the scout images (i.e., the sagittal view image 351, the coronal view image 352, and the axial view image 353) by using an MR signal that is received from an object.

In operation S333, the display 120 may perform display on the scout image so that at least one of slices is distinguished from other slices. For example, as shown in the sagittal view image 351 of FIG. 3, the display 120 may perform display so that at least one of the slices 354 is distinguished from other slices. For example, the display 120 may display a first slice with a dashed line, as shown in the sagittal view image 351 of FIG. 6. For example, the display 120 may perform display so that the first slice has a transparency that is different from those of other slices.

For example, the display 120 may display the first slice in a red color and a second slice in a yellow color, but this is not limiting. For example, the display 120 may display the first slice with a dashed line and the second slice with a solid line.

For example, the display 120 may display the first slice with a relatively thick line and the second slice with a relatively thin line. For example, when two or more slices are selected, the display 120 may differently display the two or more slices according to an order in which the two or more slices are selected.

In operations S350, S370, and S390, the input interface 110 may receive a user input corresponding to the real-time image 355 and the scout images and may update the real-time image 355 based on the user input, and the display 120 may display the updated real-time image.

Figure 8:
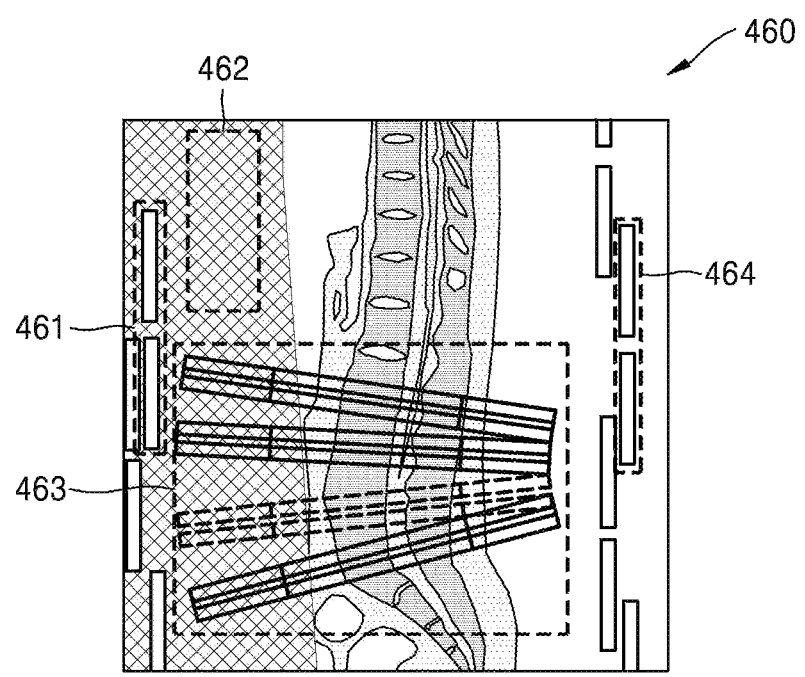
FIG. 8 is a view illustrating a scout image according to an exemplary embodiment.

FIG. 8 is a view illustrating a scout image 460 according to an exemplary embodiment.

The scout image 460 may include coil images 461 and 464. An operator may detect a relative position of a coil with respect to an object by using the coil images 461 and 464 that are included in the scout image 460.

The scout image 460 may include a saturator image 462. The operator may more obtain an image of the object with a better quality by controlling the display without the saturator image 462 that is unrelated to the object, i.e., by controlling to exclude the saturator from the image. However, this is only an example, and the operator may control the display to selectively exclude a display of any of a coil, a shim volume, and a saturator.

The scout image 460 may include a slice image 463. In addition, the scout image 460 may include a shim volume image. A user may more easily plan an imaging procedure by using at least one object image of at least one of a coil, a shim volume, a slice, and a saturator.

Figure 9:
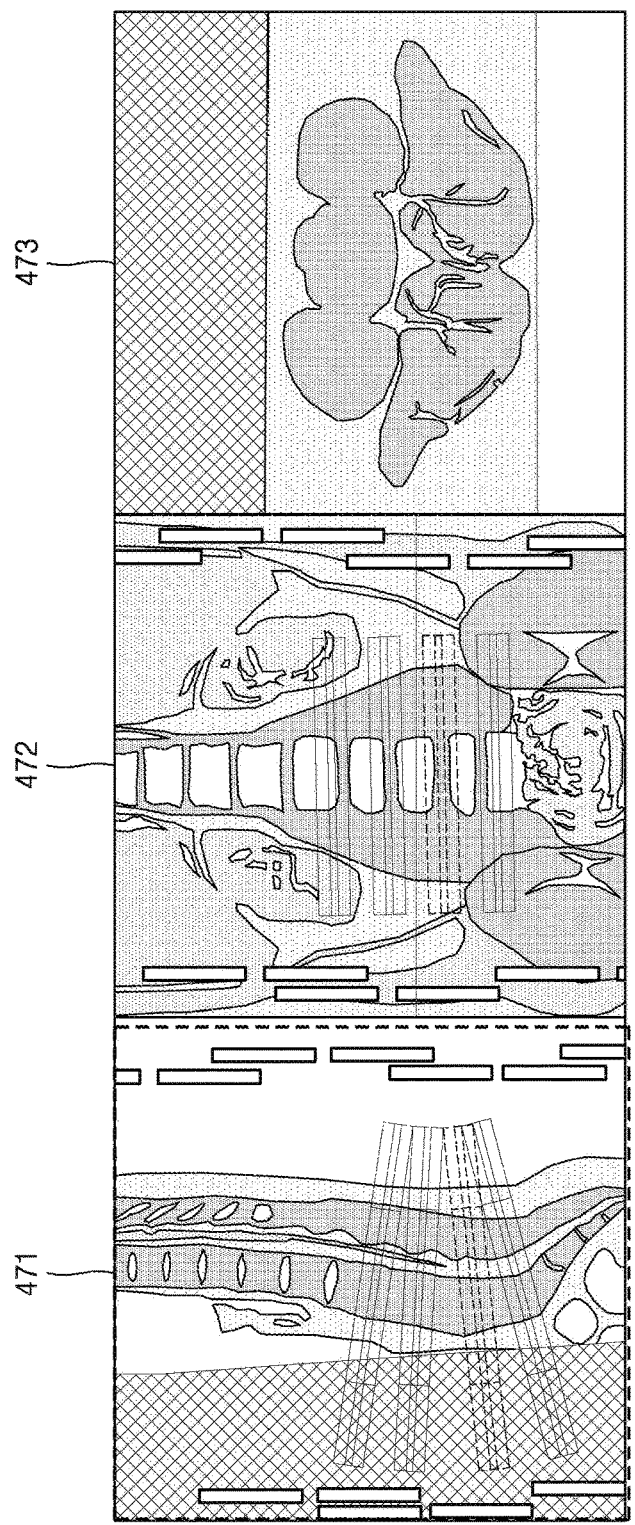
FIG. 9 is a view illustrating scout images according to an exemplary embodiment.

FIG. 9 is a view illustrating scout images according to an exemplary embodiment.

The scout images may include a sagittal view image 471, a coronal view image 472, and an axial view image 473. The sagittal view image 471, the coronal view image 472, and the axial view image 473 may respectively include object images of a coil, a shim volume, a slice, and a saturator. An operator may plan an imaging procedure by manipulating the object images. For example, the operator may set the saturator and may set an area that is not included in a real-time image. The operator may set the shim volume by using a touch or a click and may set a size, a shape, and a type of the shim volume by using any of various methods.

Figure 10:
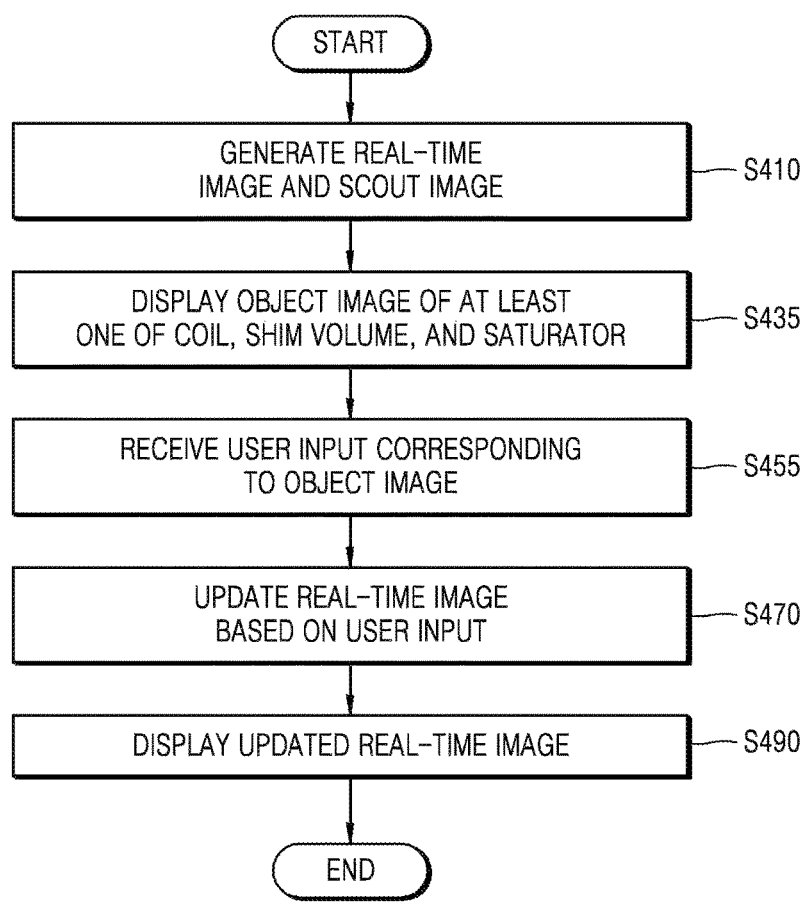
FIG. 10 is a flowchart of a method performed by the MRI apparatus to generate an MR image, according to an exemplary embodiment.

FIG. 10 is a flowchart of a method performed by the MRI apparatus 100 to generate an MR image, according to an exemplary embodiment.

Operations S410, S470, and S490 of FIG. 10 are respectively the same as operations S110, S170, and S190 of FIG. 3, and thus a repeated explanation thereof will be omitted.

Referring to FIGS. 8 through 10, in operation S410, the image processor 130 may generate a real-time image and the scout image 460 by using an MR signal that is received from an object.

In operation S435, the display 120 may display an object image of at least one of a coil, a shim volume, and a saturator. The display 120 may display various object images by using the scout image 460.

For example, the scout image 460 may include the coil images 461 and 464. An operator may detect a relative position of a coil with respect to the object by using the coil images 461 and 464 that are included in the scout image 460.

For example, the scout image 460 may include the saturator image 462. The operator may more clearly obtain an image of the object by performing display without the saturator image 462 that is unrelated to the object.

For example, the scout image 460 may include the slice image 463. In addition, the scout image 460 may include a shim volume image. The operator may more easily plan an imaging procedure by using object images of the coil, the shim volume, a slice, and the saturator.

In operation S455, the input interface 110 may receive a user input corresponding to each object image.

For example, the operator may change a size, a position, a display method, and a type of each object image by using the input interface 110. For example, the operator may change a size of the saturator by using the input interface 110.

In operations S470 and S490, the image processor 130 may update the real-time image based on the user input, and the display 120 may display the updated real-time image. For example, the display 120 may receive an input by which a size and a shape of the saturator are changed and may display the real-time image that is updated based on the input.

Figure 11:
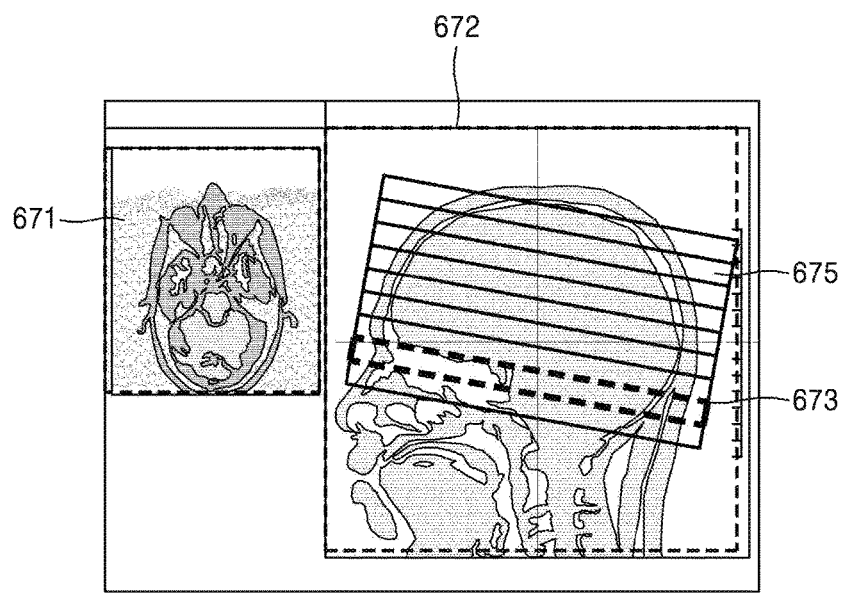
FIG. 11 is a view illustrating a real-time image and a scout image according to an exemplary embodiment.

FIG. 11 is a view illustrating a real-time image 671 and a scout image 672 according to an exemplary embodiment.

For example, when noise is included in an MR signal due to any of various artifacts, the display 120 of the MRI apparatus 100 may display an unclear image, e.g., as shown on the real-time image 671. The display 120 may perform display so that a slice 673 in which noise is included is distinguished from other slices. The display 120 may perform display on the scout image 672 so that at least one of a transparency, a color, and a thickness of the slice 673 in which noise is included is distinguished from those of the slices 675 in which noise is not included.

Figure 12:
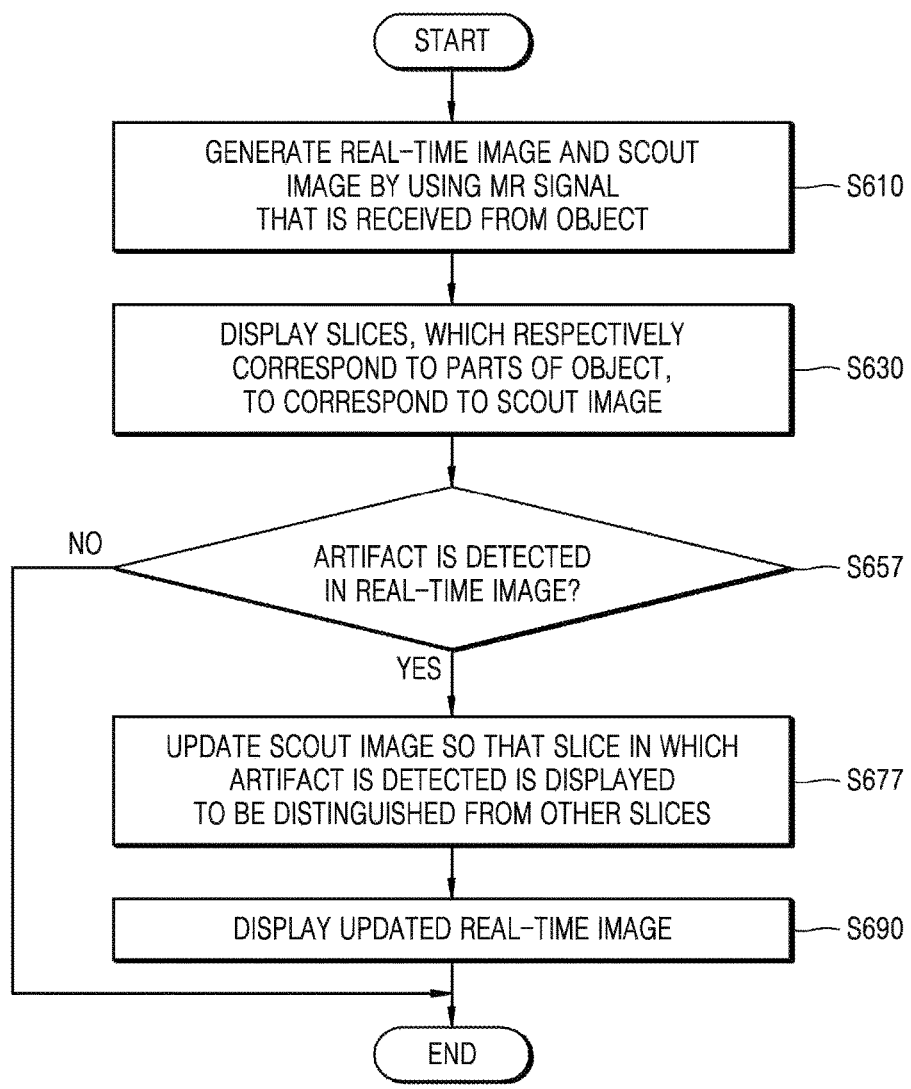
FIG. 12 is a flowchart of a method performed by the MRI apparatus to generate an MR image, according to an exemplary embodiment.

FIG. 12 is a flowchart of a method performed by the MRI apparatus 100 to generate an MR image, according to an exemplary embodiment.

Operations S610, S630, and S690 of FIG. 12 are respectively the same as operations S110, S130, and S190 of FIG. 3, and thus a repeated explanation thereof will be omitted.

Referring to FIGS. 11 and 12, in operation S610, the image processor 130 may generate the real-time image 671 and the scout image 672 by using an MR signal that is received from an object. In operation S630, the display 120 may display the slices 673 that respectively correspond to parts of the object to correspond to the scout image 672.

In operation S657, the image processor 130 may determine whether an artifact is detected in the real-time image 671. When it is determined in operation S657 that an artifact is detected in the real-time image 671, the image processor 130 may update the real-time image 671.

In operation S677, the image processor 130 may update the scout image 672 so that a slice in which a user artifact is detected is displayed to be distinguished from other slices. In operation S690, the display 120 may display the updated real-time image.

In another exemplary embodiment, when an SAR or a PNS that is measured when the real-time image 671 is generated or updated exceeds a reference value, the image processor 130 may update the scout image 672 by making a mark corresponding to the exceeding of the reference value on the scout image 672.

Figure 13A:
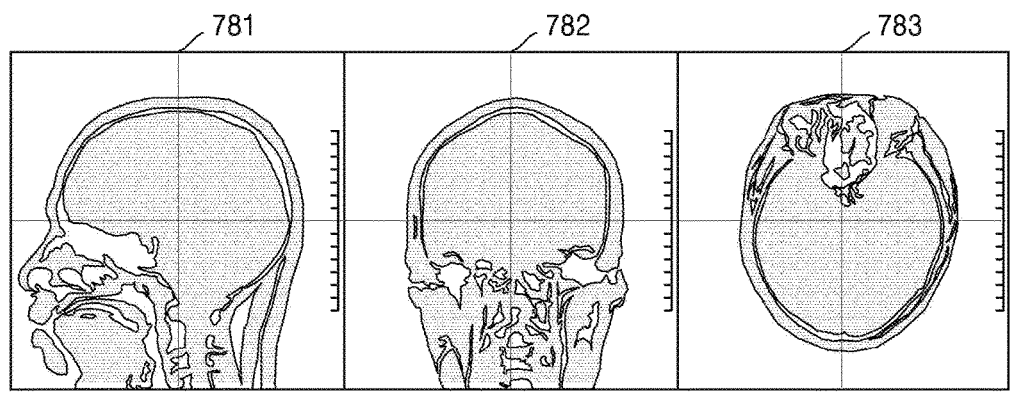
FIGS. 13A and 13B are views for explaining an operation of changing an arrangement of scout images, according to an exemplary embodiment.
Figure 13B:
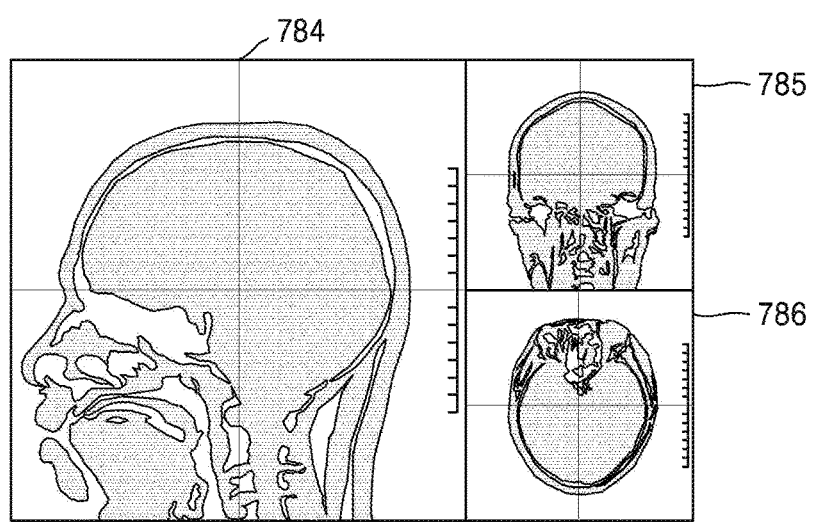
Figure 14:
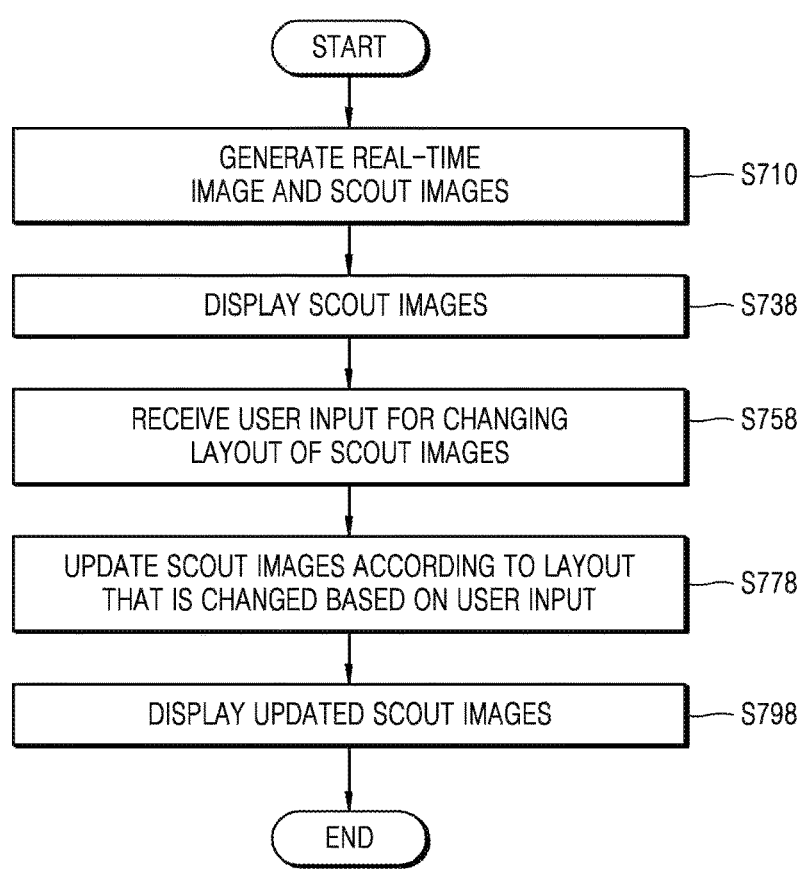
FIG. 14 is a flowchart for explaining an operation of changing an arrangement of scout images, according to an exemplary embodiment.

FIGS. 13A and 13B are views for explaining an operation of changing an arrangement of scout images, according to an exemplary embodiment. FIG. 14 is a flowchart for explaining an operation of changing an arrangement of scout images, according to an exemplary embodiment.

Referring to FIGS. 13A through 14, in operation S710, the image processor 130 may generate scout images 781, 782, and 783 by using an MR signal that is received from an object. In operation S738, the display 120 may display the scout images 781, 782, and 783.

In operation S758, the input interface 110 may receive a user input for changing a layout of the scout images 781, 782, and 783. The input interface 110 may receive an input by using any of various methods. For example, an operator may re-arrange the scout images 781, 782, and 783 by using a drag and drop method. For example, the operator may input sizes and positions of the scout images 781, 782, and 783. For example, the operator may select one layout among layouts suggested by the MRI apparatus 100 and may re-arrange the scout images 781, 782, and 783.

In operation S778, the image processor 130 may update the scout images 781, 782, and 783 according to the layout that is changed based on the user input.

For example, the image processor 130 may update the scout images 781, 782, and 783 and may arrange scout images 784, 785, and 786 to have a layout shown in FIG. 13B.

In operation S798, the display 120 may display the updated scout images 784, 785, and 786.

For example, the display 120 may display the scout images 784, 785, and 786 having the layout that are updated to correspond to the user input.

Figure 15A:
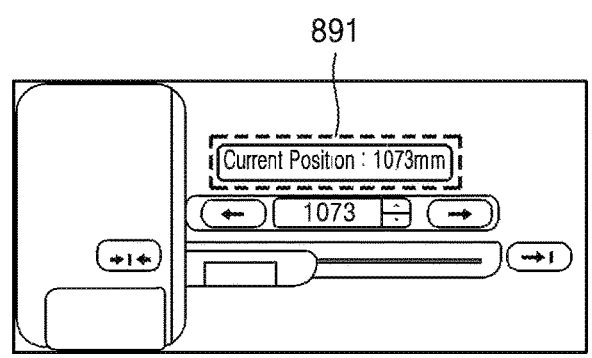
FIGS. 15A and 15B are views for explaining a method performed by an input interface, according to an exemplary embodiment.
Figure 15B:
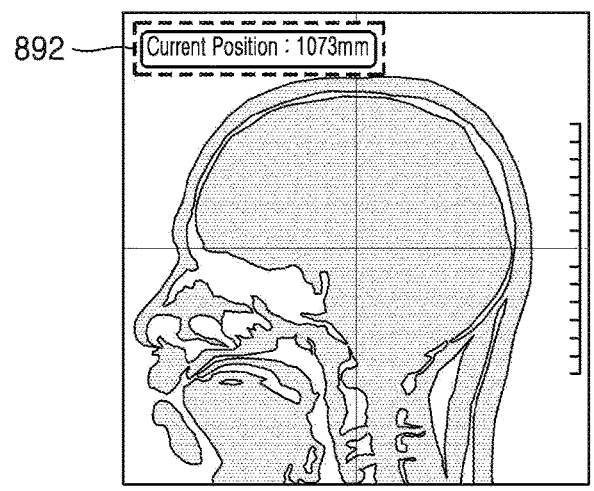

FIGS. 15A and 15B are views for explaining a method performed by the input interface 110 to receive position information of a table in order to adjust a position of an object, according to an exemplary embodiment.

Referring to FIG. 15A, the input interface 110 may receive position information of a table that supports the object. The MRI apparatus 100 may adjust the position of the table in order to adjust a point of interest of an operator. The input interface 110 may be a GUI 891 as shown in FIG. 15A.

For example, the display 120 may display current position information of the table, and the input interface 110 may receive the corrected position information of the table. The position information of the table may be expressed by using a distance between a reference point (e.g., an edge portion of the table) and a measurement point (e.g., an imaging point). For example, the position information of the table may be expressed by using plane coordinates or spatial coordinates. The operator may correct the position of the table by using the GUI 891.

Referring to FIG. 15B, the display 120 may display position information of the table in a scout image. The display 120 may display the position information of the table by using, for example, a popup window 892, on a portion of the scout image.

The above-described exemplary embodiments may be implemented as an executable program, and may be executed by a computer by using a computer-readable recording medium.

Examples of the computer-readable recording medium include magnetic storage media (e.g., ROM, floppy disks, hard disks, etc.), optical recording media (e.g., CD-ROMs or DVDs), etc.

The foregoing exemplary embodiments and advantages are merely exemplary and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A magnetic resonance imaging (MRI) apparatus comprising:
    an image processor configured to generate a real-time image and a scout image based on an MR signal that is obtained from an object;
    a display configured to display slices, which respectively correspond to portions of the object, on the scout image and to display the real-time image; and
    an input interface configured to receive a first user input selecting at least one slice among the slices displayed in the scout image, the first user input corresponding to a user command to change a displaying property of the at least one slice to be displayed distinguishably from non-selected slices in the scout image,
    wherein the image processor is further configured to update the real-time image, so that a displaying property of the real-time image, which has been previously displayed, is changed based on the first user input, and
    the display is further configured to display the updated real-time image having the changed displaying property in correspondence with the user command with respect to the displaying property of the at least one slice displayed in the scout image, and to display the slices on the scout image so that the at least one slice is displayed differently from the non-selected slices.

2. The MRI apparatus of claim 1, wherein the first user input is the user command for adjusting at least one among a position, a size, a direction, and a luminosity of the at least one slice in the scout image.

3. The MRI apparatus of claim 1, wherein the scout image comprises extraneous images of a coil, a shim volume, and a saturator,
    the input interface is further configured to receive a second user input for at least one of the extraneous images, and
    the display is further configured to perform a display so that the at least one of the extraneous images, which is selected by the second user input, is distinguished from other extraneous images.

4. The MRI apparatus of claim 1, wherein the display is further configured to display, on the scout image, a mark corresponding to an artifact in the real-time image.

5. The MRI apparatus of claim 1, wherein a value of a specific absorption rate (SAR) or a peripheral nervous stimulus (PNS) is measured when the real-time image is updated, and
in response to the value exceeding a reference value, the display is further configured to display a mark corresponding to exceeding of the reference value, on the scout image.

6. The MRI apparatus of claim 1, wherein the input interface is further configured to receive a second user input corresponding to the scout image,
the scout image comprises a sagittal view image, a coronal view image, and an axial view image, and
at least one of an arrangement of the sagittal view image, the coronal view image, and the axial view image or a size of at least one among the sagittal view image, the coronal view image, and the axial view image is changed by the second user input.

7. The MRI apparatus of claim 1, wherein the display is further configured to display, on the scout image, position information of a table that supports the object in the MRI apparatus.

8. The MRI apparatus of claim 1, wherein the image processor is further configured to adjust a brightness of a portion of the real-time image and a brightness of the at least one slice of the scout image, based on the first user input, and
the display is further configured to display the updated real-time image having the portion with the adjusted brightness, and to display the slices on the scout image so that the at least one slice is displayed with the brightness which is different from the brightness of the non-selected slices.

9. A method of generating a magnetic resonance (MR) image by a magnetic resonance imaging (MRI) apparatus, the method comprising:
generating a real-time image and a scout image based on an MR signal that is obtained from an object;
displaying the real-time image;
displaying slices, which respectively correspond to portions of the object, on the scout image;
receiving a first user input selecting at least one slice among the slices displayed in the scout image, the first user input corresponding to a user command to change a displaying property of the at least one slice to be displayed distinguishably from non-selected slices in the scout image;
updating the real-time image, so that a displaying property of the real-time image, which has been previously displayed, is changed based on the first user input;
displaying the updated real-time image having the changed displaying property in correspondence with the user command with respect to the displaying property of the at least one slice displayed in the scout image; and
displaying the slices on the scout image so that the at least one slice is displayed differently from the non-selected slices.

10. The method of claim 9, wherein the displaying the slices on the scout image comprises:
displaying lines which separate the slices from one another; and
displaying the slices so that at least one of the lines is distinguished from other lines.

11. The method of claim 10, wherein at least one among a transparency, a color, and a shape of the at least one of the lines is displayed to be different from that of the other lines.

12. The method of claim 9, wherein the first user input is the user command for adjusting at least one among a position, a size, a direction, and a luminosity of the at least one slice on the scout image.

13. The method of claim 9, wherein the scout image comprises extraneous images of a coil, a shim volume, and a saturator, and
at least one of the extraneous images is displayed to be distinguished from other extraneous images, in response to receiving a second user input selecting the at least one of the extraneous images.

14. The method of claim 13, wherein the second user input is received through a shortcut key that is preset.

15. The method of claim 9, further comprising:
receiving a second user input being a selection input of another slice among the slices;
obtaining the real-time image of the another slice; and
displaying a portion of the scout image corresponding to the another slice to be distinguished from portions of the scout image corresponding to other slices.

16. The method of claim 9, wherein the displaying the updated real-time image comprises:
in response to an artifact being detected in the updated real-time image, displaying a mark corresponding to the artifact on a corresponding slice displayed on the scout image, among the slices.

17. The method of claim 9, wherein the displaying the updated real-time image comprises:
in response to a specific absorption rate (SAR) or a peripheral nervous stimulus (PNS) that is measured when the real-time image is updated exceeding a reference value, displaying a mark corresponding to exceeding of the reference value on the scout image.

18. The method of claim 9, wherein the scout image comprises a sagittal view image, a coronal view image, and an axial view image, and
the method further comprises:
receiving a second user input, and
changing at least one of an arrangement of the sagittal view image, the coronal view image, and the axial view image or a size of at least one among the sagittal view image, the coronal view image, and the axial view image.

19. The method of claim 9, further comprising:
displaying, on the scout image, position information of a table that supports the object in the MRI apparatus.

20. The method of claim 9, wherein the updating the real-time image comprises adjusting a brightness of a portion of the real-time image and a brightness of the at least one slice of the scout image, based on the first user input,
the displaying the updated real-time image comprises displaying the updated real-time image having the portion with the adjusted brightness, and
the displaying the slices on the scout image comprises displaying the slices so that the at least one slice is displayed with the brightness which is different from the brightness of the non-selected slices.

21. The MRI apparatus of claim 1, wherein the input interface is further configured to receive a second user input with respect to the real-time image.

* * * * *